(12) United States Patent
Hoerner

(10) Patent No.: US 6,361,568 B1
(45) Date of Patent: Mar. 26, 2002

(54) PROSTHETIC SLEEVE WITH AIR OUTLET VALVE

(75) Inventor: Jeffrey S. Hoerner, Manchester, NH (US)

(73) Assignee: Alps South Corporation, St. Petersburg, FL (US)

( * ) Notice: Subject to any disclaimer, the term of this patent is extended or adjusted under 35 U.S.C. 154(b) by 0 days.

(21) Appl. No.: 09/501,036

(22) Filed: Feb. 9, 2000

Related U.S. Application Data

(60) Provisional application No. 60/119,296, filed on Feb. 9, 1999, and provisional application No. 60/157,765, filed on Oct. 5, 1999.

(51) Int. Cl.$^7$ .................................................. A61F 2/60
(52) U.S. Cl. ......................................................... 623/32
(58) Field of Search ............................ 623/34, 33, 36, 623/32; 602/62, 63, 77

(56) References Cited

U.S. PATENT DOCUMENTS

| | | | |
|---|---|---|---|
| 1,586,015 A | * | 5/1926 | Underwood |
| 2,790,180 A | | 4/1957 | Hauser |
| 2,808,593 A | | 10/1957 | Andersen |
| 3,309,714 A | | 3/1967 | Porten |
| 3,671,980 A | | 6/1972 | Baird |
| 3,889,301 A | | 6/1975 | Bonner, Sr. |
| 4,146,021 A | * | 3/1979 | Brosseau et al. ............. 128/75 |
| 4,300,245 A | | 11/1981 | Saunders |
| 4,468,821 A | | 9/1984 | Saunders |
| 4,595,172 A | | 6/1986 | Henderson |
| 4,655,779 A | | 4/1987 | Janowiak |
| 4,685,453 A | * | 8/1987 | Guignard et al. ............. 128/90 |
| 4,822,371 A | | 4/1989 | Jolly et al. |
| 5,108,456 A | * | 4/1992 | Coonan, III ................. 623/37 |
| 5,139,523 A | | 8/1992 | Paton et al. |
| 5,201,774 A | | 4/1993 | Greene |
| 5,376,129 A | | 12/1994 | Faulkner et al. |
| 5,534,034 A | * | 7/1996 | Caspers ....................... 623/32 |
| 5,702,489 A | | 12/1997 | Slemker |
| 5,728,170 A | | 3/1998 | Becker |

* cited by examiner

*Primary Examiner*—Bruce Snow
(74) *Attorney, Agent, or Firm*—Ronald E. Smith; Smith & Hopen, P.A.

(57) ABSTRACT

A prosthetic device having a socket adapted to receive an amputee's limb is provided. A sleeve is adapted to overlap the juncture between the socket and the amputee's limb. The sleeve includes an air outlet valve to permit air to escape when the amputee's limb is inserted into the sleeve. Preferably, the sleeve is a resilient air-permeable member that creates a partial vacuum between the limb and the socket to securely retain the prosthetic device to the amputee's limb. The sleeve and valve arrangement of the present invention permits an amputee to comfortably and effectively wear a prosthetic device.

7 Claims, 2 Drawing Sheets

PROSTHETIC SLEEVE WITH AIR OUTLET VALVE

RELATED APPLICATION

This application claims priority to provisional application Nos. 60/119,296 and 60/157,765 filed on Feb. 9, 1999 and Oct. 5, 1999, respectively.

BACKGROUND OF THE INVENTION

This invention relates to an apparatus for securing a prosthetic device to an amputee's limb, specifically, the invention relates to a prosthetic sleeve having a valve for securing the prosthetic device to the amputee's limb.

By way of background, prosthetic devices for amputees generally include a socket for engaging the amputee's limb and a prosthetic limb joined to the socket. One way to secure the socket to the amputee's limb is to provide a resilient, air-impermeable sleeve that overlaps the juncture between the limb and the socket. When the limb is inserted into the socket, air is forced out of the socket to create a partial vacuum between the limb and the socket. The sleeve is then rolled over the limb and provides a seal to prevent air from re-entering the socket and disrupting the vacuum. Thus, the resilient sleeve joins the limb and socket together by maintaining the partial vacuum within the socket. The resilient sleeve also grips the socket and the leg to resist removal of the socket from the leg.

To create the vacuum, air must be allowed to escape from the socket as the amputee's limb is inserted therein. Many prosthetic sockets include an outlet valve at the bottom of the socket to allow as much air as possible to escape during insertion of the amputee's limb. The valve arrangements of the prior art utilize many components and have been rather complex. Furthermore, an air outlet at the bottom of the socket can interfere with the attachment of the prosthetic limb to the socket which may compromise the comfort and effectiveness of the prosthetic device. The present invention overcomes this problem by incorporating a one-way air outlet valve into the resilient sleeve.

SUMMARY OF THE INVENTION AND ADVANTAGES

The prosthetic device of the present invention includes a socket adapted to receive an amputee's limb. A sleeve is adapted to overlap the juncture between the socket and the amputee's limb. The sleeve includes an air outlet valve to permit air to escape when the amputee's limb is inserted into the sleeve. Preferably, the sleeve is a resilient air-permeable member that creates a partial vacuum between the limb and the socket to securely retain the prosthetic device to the amputee's limb. The sleeve and valve arrangement of the present invention permit an amputee to comfortably and effectively wear a prosthetic device.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENT

Figures 1, 3:
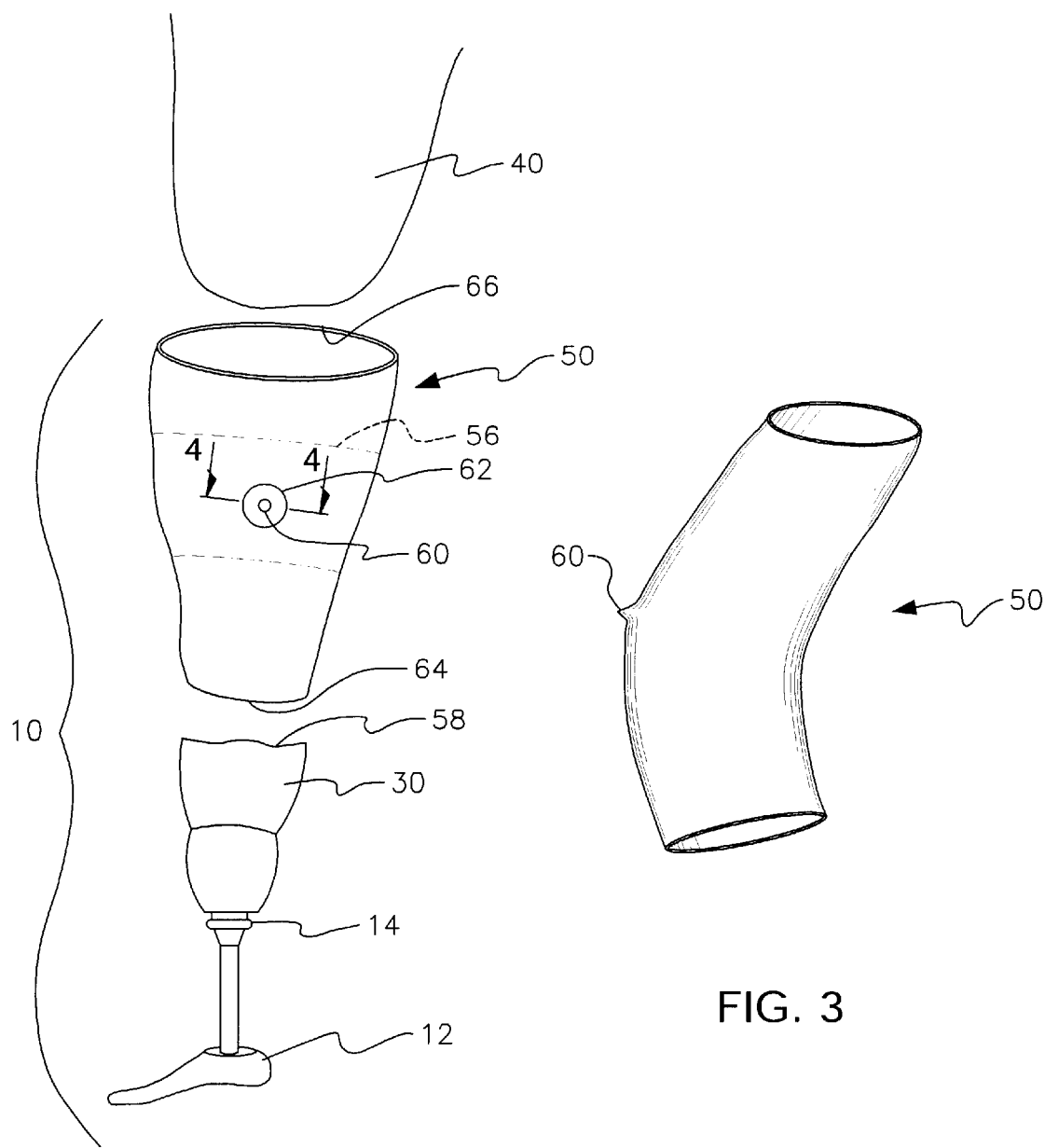
FIG. 1 is a front perspective view of the present invention prosthetic sleeve used in conjunction with a prosthetic device and an amputee's limb.
FIG. 3 is a side perspective view of the present invention prosthetic sleeve.

Referring to the Figures, a prosthetic device is generally shown at 10 in FIG. 1. The prosthetic device 10 includes a socket 30 for receiving an amputee's limb 40 and a sleeve 50 adapted to secure the socket 30 to the amputee's limb 40. Typically, the socket 30 is made of a rigid material such as a carbon reinforced plastic. A prosthetic limb 12 is joined to the socket 30 by an attachment device 14 of the type commonly known to those of skill in the art.

Figure 2:
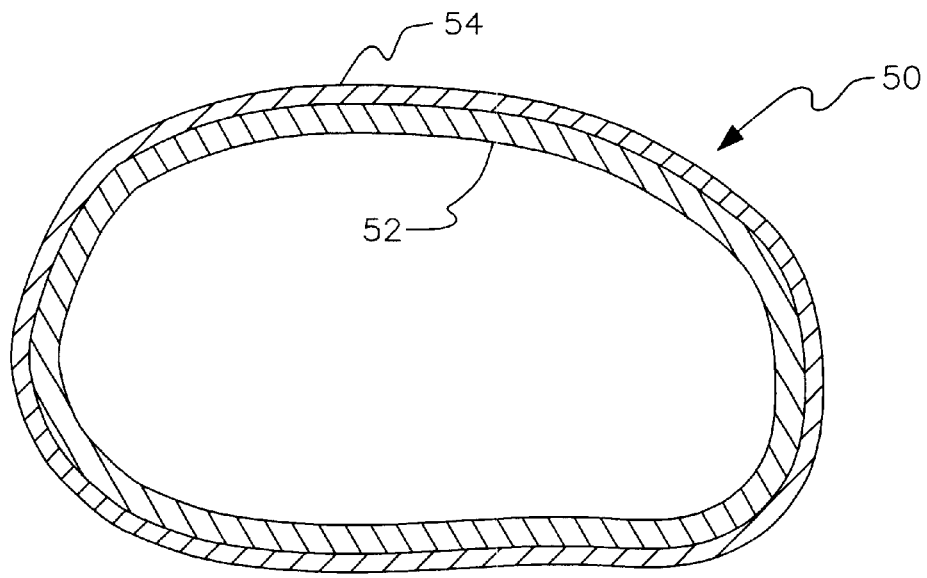
FIG. 2 is a cross-sectional view of the present invention taken along line 2—2 in FIG. 1.

As shown in FIG. 2, the sleeve 50 comprises a multi-layered tube including an inner layer 52 of resilient material such as thermoplastic elastomer, silicone, neoprene, urethane, or latex to allow the sleeve 50 to fit intimately with the limb 40 and the socket 30. Neoprene is a more common material used to form sleeves 50 of this type, but any of the listed materials or other suitable materials will work effectively. An outer fabric layer 54 is joined to the resilient material layer 52 of the sleeve 50 to provide a smooth outer surface to the sleeve 50. The fabric layer 54 is made from Lycra® or another suitable low friction material.

As shown in phantom in FIG. 1, a tube-shaped panel 56 is joined to an inside surface of the sleeve 50 and extends around the inner periphery of the sleeve 50. The panel 56 is positioned at an intermediate location along the length of the sleeve 50. The panel 56 is multi-layered and includes an inner layer of neoprene or other resilient material joined to an outer layer of Lycra® or other low-friction fabric. The resilient layer of the panel 56 is joined to the resilient layer 52 of the sleeve 50.

The panel 56 is positioned to surround the upper edge 58 of the socket 30 when the socket 30 is placed within the sleeve 50. In this manner, the panel 56 will reduce the friction between the socket 30 and the sleeve 50 and prevent the socket 30 from rubbing against the resilient layer 52 of the sleeve 50. A panel 56 of this type is disclosed in U.S. Pat. No. 4,822,371 to Jolly et al., the disclosure of which is incorporated herein by reference.

A one way air expulsion valve 60 is provided in the sleeve 50 for releasing air during insertion of the limb 40 within the socket 30. A "duck-bill" valve 60 may be used, which comprises a rubber member including upper and lower lips which are manufactured with an inherent tension to remain closed until air pressure from inside the sleeve 50 opens the valve 60. However, stretching of the sleeve 50 during use can also cause the valve 60 to open unexpectedly, allowing air to re-enter the socket 30 and disrupt the vacuum created between the limb 40 and the socket 30. To minimize this effect, a reinforcing patch 62 of flexible, non-resilient material such as Dacron® is applied to the sleeve 50 surrounding the valve 60. The patch 62 will reduce the stresses placed on the valve 60 during use of the sleeve 50, minimizing the chance that the valve 60 will open undesirably.

FIG. 3 shows a side view of the prosthetic sleeve 50 and outlet valve 60. As discussed above, the air outlet valve 60 allows air to be forced out of the socket 30 by the limb 40, promoting an almost complete vacuum to secure the socket 30 to the limb 40. Any type of mechanism positioned on the sleeve 50 may be used to release the air within the socket 30 and sleeve 50. Preferably, a one-way check valve is used to allow air to automatically escape while preventing reentry of the air. It is also possible to use a manually controllable valve to allow the user to control the amount of air allowed to escape and, consequently, the strength of the vacuum.

Figure 4:
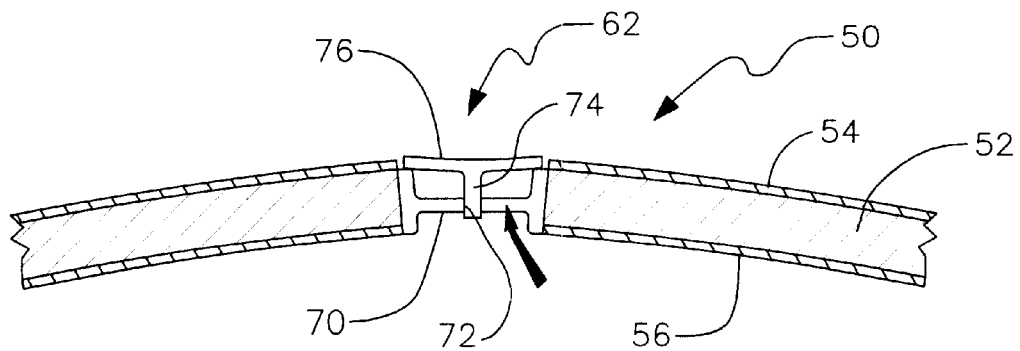
FIG. 4 is a cross-sectional view of the prosthetic sleeve taken along line 4—4 in FIG. 3.

Preferably, a flapper valve is used to release air from the prosthetic sleeve because it has a low profile, as shown in FIG. 4. Flapper valve 62 has a circular housing 70 with an H-shaped cross-section. Housing 70 has at least one passageway through it (not shown) that permits air to travel from one side of the housing to the other. Housing 70 further includes a hole 72 that receives a stem of a rubber flapper 76. Flapper 76 is installed in housing 70 so that the perimeter of flapper 76 seats against housing 70, as shown in FIG. 4. As air is being forced out of the interior of prosthetic sleeve 50 (depicted by the arrow), the perimeter of flapper 76 disengages from housing 70 thereby permitting air to escape. Once a vacuum is created, flapper 76 is drawn inward to the position shown in FIG. 4.

To install prosthetic device 10 on residual limb 40, a lower portion 64 of sleeve 50 is positioned over socket 30. However, it is to be understood that the sleeve may be integrally formed with the prosthetic device. Top 66 of sleeve 50 is then rolled down so that limb 40 may be more easily placed into socket 30. Once limb 40 is placed into socket 30, top 66 of sleeve 50 is rolled upward to overlap the juncture between limb 40 and socket 30. As the user places weight on limb 40, air within socket 30 is compressed and attempts to escape through sleeve 50. Valve 60 or 62 permits air to escape as residual limb 40 is being firmly seated within socket 30.

Valve 60 or 62 is preferably disposed on sleeve 50 at a location corresponding to panel 56. In other words, valve 60 or 62 provides an air passage through both panel 56 and sleeve 50. Panel 56 provides the added benefit of improving the ease with which air can pass from socket 30 to valve 60 or 62. Without panel 56, resilient inner layer 53 of sleeve 50 grips socket 30 and forms a seal between the upper edge of socket 30 and residual limb 40. As such, it is more difficult for air to travel from upper edge 58 of socket 30 to valve 60 or 62 unless valve 60 or 62 is coincidentally positioned precisely at upper edge 58 of socket 30. Panel 56 prevents a seal from forming at upper edge 58 of socket 30, allowing air to more easily travel to valve 60 or 62. Further, the outer fabric layer of panel 56 is air-permeable, forming an air passage from upper edge 58 of socket 30 to valve 60 or 62. In other words, the fabric layer of panel 56 "wicks" the air away from upper edge 58 of socket 30 to valve 60 or 62.

The invention has been described in illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. An apparatus for securing a prosthetic device having a socket with an exterior surface to a residual limb, comprising:

a tubular sleeve adapted to overlap the juncture between the residual limb and the socket covering at least a portion of the limb and at least a portion of the exterior surface; and said sleeve including an air outlet one-way valve.

2. The apparatus of claim 1 wherein said sleeve is resilient.

3. The apparatus of claim 2 further comprising an air-permeable fabric panel joined to an inner surface of said sleeve at an intermediate location along the length of said sleeve for reducing friction between said prosthetic device and said apparatus.

4. The apparatus of claim 3 wherein said valve is disposed through said sleeve and through said panel.

5. The apparatus of claim 1 wherein the one-way valve is a flapper valve.

6. The apparatus of claim 1 further comprising a reinforcing patch joined to said sleeve and surrounding said valve.

7. A prosthetic sleeve for securing a prosthetic device with a prosthetic limb to an amputee's limb comprising:

a resilient tubular member having an opening adapted to receive the amputee's limb and an end opposite said opening adapted for connection to the prosthetic limb, said tubular member having an interior surface;

a panel disposed within said tubular member and secured to said inner surface; and an air outlet valve extending through said tubular member and said panel to permit air to flow through said tubular member and said panel.

* * * * *